(12) United States Patent
Maddison

(10) Patent No.: US 12,044,688 B1
(45) Date of Patent: Jul. 23, 2024

(54) HOME PREGNANCY PROGRESSION TESTING SYSTEM AND METHOD

(71) Applicant: Sarah Maddison, Raleigh, NC (US)

(72) Inventor: Sarah Maddison, Raleigh, NC (US)

( * ) Notice: Subject to any disclaimer, the term of this patent is extended or adjusted under 35 U.S.C. 154(b) by 245 days.

(21) Appl. No.: 17/133,213

(22) Filed: Dec. 23, 2020

(51) Int. Cl.
  *G01N 33/68* (2006.01)
  *G01N 33/563* (2006.01)
  *G01N 33/76* (2006.01)

(52) U.S. Cl.
  CPC ......... *G01N 33/689* (2013.01); *G01N 33/563* (2013.01); *G01N 33/76* (2013.01)

(58) Field of Classification Search
  None
  See application file for complete search history.

(56) References Cited

U.S. PATENT DOCUMENTS

| | | | | |
|---|---|---|---|---|
| 2010/0129935 | A1* | 5/2010 | Maddison | G01N 33/76 422/400 |
| 2018/0088136 | A1* | 3/2018 | Saji | G01N 33/76 |

OTHER PUBLICATIONS

Davies et al., Clin Lab Med 23 (2003) 257-264 (Year: 2003).*
Danielle Betz and Kathleen Fane, NCBI Bookshelf., National Library of Medicine, National Institutes of Health. StatPearls [Internet]. Treasure Island (FL): StatPearls Publishing; updated Aug. 14, 2023 (Year: 2023).*
P. Berger and A.J. Lapthorn, Molecular Immunology 76 (2016) 134-145 (Year: 2016).*

* cited by examiner

*Primary Examiner* — Christina M Borgeest
(74) *Attorney, Agent, or Firm* — Avek IP, LLC

(57) ABSTRACT

A pregnancy progression test system that includes multiple tests, each with decreasing sensitivity to provide the user of indication of a progressing pregnancy when taken over the course of a time period.

2 Claims, 5 Drawing Sheets

HOME PREGNANCY PROGRESSION TESTING SYSTEM AND METHOD

BACKGROUND

1. Field of the Invention

The present invention relates to a simple home testing method for confirming a viable pregnancy. In particular the present invention relates to testing an individual over two or more periods to determine if the key pregnancy hormone is increasing thus indicating a successful pregnancy. Furthermore, when the hormone is noted not to rise appropriately, the individual can be alerted to the possibility of a miscarriage and/or ectopic (tubal) pregnancy.

2. Description of Related Art

Home pregnancy tests are well known in the art and provide women a first indicator of pregnancy. These are generally achieved through a urine test in the comfort of the user's home, wherein the user is provided with either a positive or negative result. A positive result indicates that a chemical in the urine that is associated with pregnancy is found, however, it does not always indicate a pregnancy and further does not indicate whether the pregnancy is progressing. The most commonly used marker is hCG, the human chorionic gonadotropin, originally discovered in 1930 to be produced by the placenta during pregnancy and excreted into the urine.

It is known that hCG is produced by trophoblast cells of the placenta in pregnancy. It is also produced in gestational trophoblastic diseases (hydatidiform mole, choriocarcinoma, and placental site trophoblastic tumors) and in testicular germ cell malignancies. The complete hCG protein is a glycoprotein composed of 2 dissimilar subunits, an alpha and beta subunit, held together by charge interactions. The hCG beta subunit is composed of 92 amino acids and contains 2 N-linked oligosaccharides. The hCG alpha subunit is composed of 145 amino acids and contains 2 N-linked and 4 O-linked oligosaccharides. The 8 oligosaccharide side chains comprise greater than 30% of the molecular weight of hCG, making it an exceptionally highly glycosylated glycoprotein. The beta subunit is the primary unit being detected in home pregnancy testing units. The beta hCG rises in a predictable logarithmic pattern in early pregnancy.

Over 40 professional laboratory serum hCG tests, approximately 30 point of care serum and urine hCG tests and a similar number of home pregnancy tests are sold today for detecting hCG and for establishing the onset of pregnancy. Whether intended for professional laboratory or home use, today all pregnancy tests work on the multi-antibody immunometric assay principal: commonly one and occasionally two antibodies (mono- or polyclonal) binds and immobilizes hCG and a second antibody, the tracer antibody, raised to a distant (different) epitope and labeled with an enzyme, dye or chemiluminescence agent, marks the presence of hCG or quantitates hCG present in the sample.

The hCG glycoprotein is a heterogeneous molecule. Cleaved or nicked forms of hCG, free subunits of hCG, and fragments of hCG are all detectable in serum and urine samples during pregnancy. Variable detection or lack of detection of cleaved molecules, free subunits and fragments is a major cause of inter-assay variation in hCG results.

The first home pregnancy testing kits, using an hCG test, were released in the mid-1970's, however, they do create false positives in spite of the fact that hCG is a reliable marker. There are a variety of products on the market that all work slightly different and have a range of sensitivities for hCG from about 20 mIU/mL to 100 mIU/mL, more or less. Problems occur with pregnancy testing in this manner for a variety of reasons including errors of test application, use of drugs containing the assay molecule and non-pregnant production of the chemical. In addition, because the sensitivity of the available home testing units for hCG varies greatly, false negatives can occur if the test is given too early. One particular problem occurs when a home pregnancy test is performed and shows a positive reading, but the individual has already miscarried or spontaneously aborted the pregnancy. The urine will still test positive for hCG, but the individual is unaware that the level has plateaued or is falling which would indicate a potential pregnancy problem. There is currently no simple home method for confirming viable pregnancy and whether the pregnancy is progressing or not.

When pregnancy viability is in question, the status of the pregnancy can be followed with serial quantitative levels that confirm the expected doubling approximately every forty-eight hours. This currently can only be achieved with consecutive blood levels, thus requiring physician and phlebotomy services.

Accordingly, although great strides have been made in the area of home pregnancy tests, many shortcomings remain.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
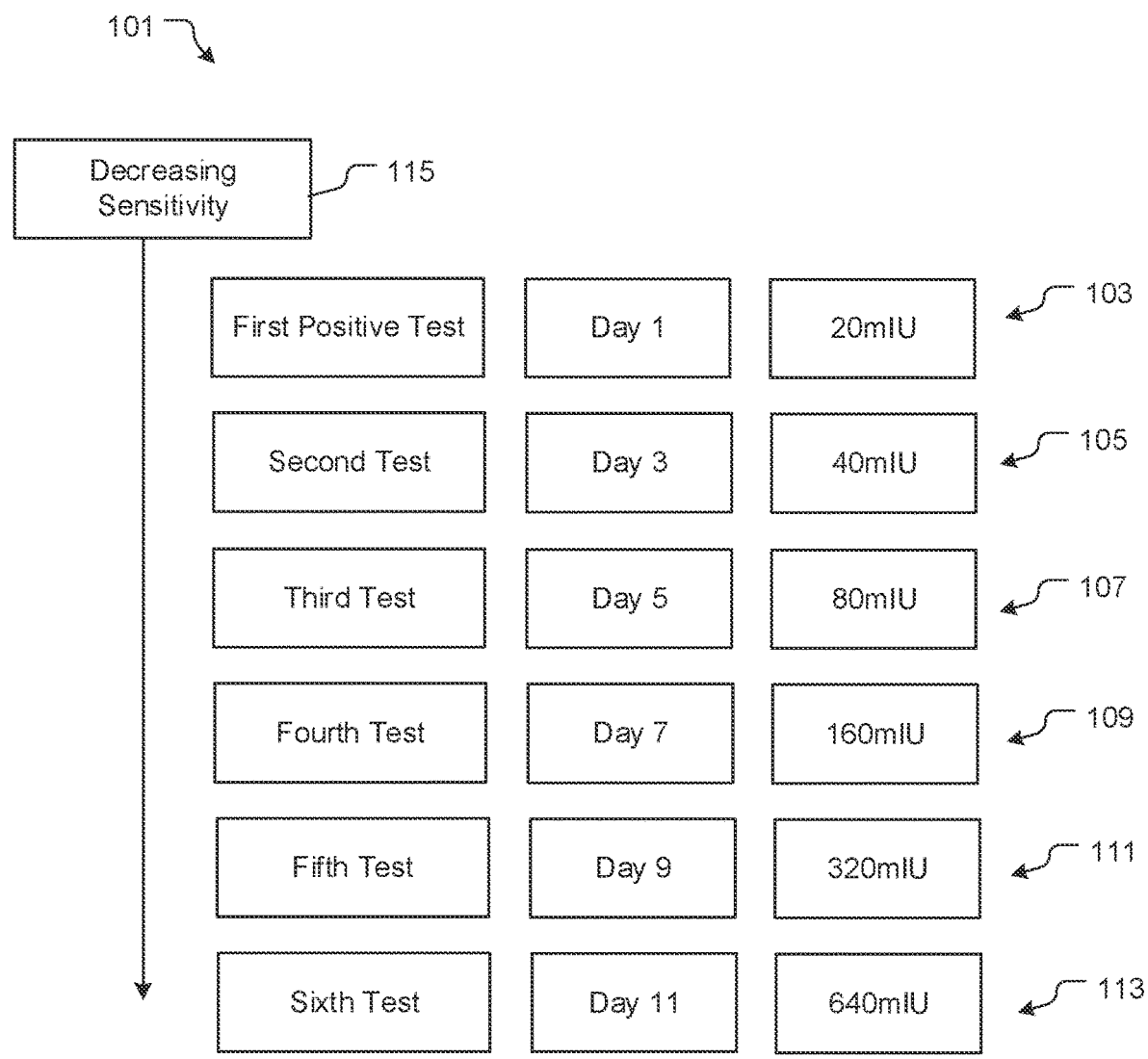
FIG. 1 is a simplified diagram of a first embodiment of home pregnancy progression testing system in accordance with the present application.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional pregnancy testing systems. Specifically, the present invention provides for a testing system that includes a plurality of tests of decreasing sensitivity, wherein the user will take a test every two days for a period of time, the receiving of positive results on each of the plurality of tests indicating a likelihood of pregnancy progression. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Referring now to the drawings wherein like reference characters identify corresponding or similar elements throughout the several views, FIG. 1 depicts a simplified diagram of a testing system 101 in accordance with a preferred embodiment of the present application. It will be appreciated that system 101 overcomes one or more of the above-listed problems commonly associated with conventional home pregnancy testing systems.

In the contemplated embodiment, system 101 includes a plurality of tests 103, 105, 107, 109, 111, 113, wherein each of the plurality of tests has a decreasing sensitivity 115 of reaction. As shown, in this embodiment, the level of hCG will need to increase in the sample provided by the user in order for the user to continuously receive positive results. The receiving of positive results indicates that the pregnancy is likely progressing. It should be appreciated and understood that hCG will increase daily during the early phase of a pregnancy, and accordingly, this increase indicates that the pregnancy is likely progressing.

It should further be appreciated that the sensitivity requirements may vary and the precise numbers are provided for example. In this exemplary embodiment, the user will begin by taking the first test with the highest sensitivity. If the user receives a positive result, this will be indicated as "Day 1". The user will then wait two days and take the "Day 3" test, wherein another positive result indicates that the user's hCG level has increased.

Figure 2:
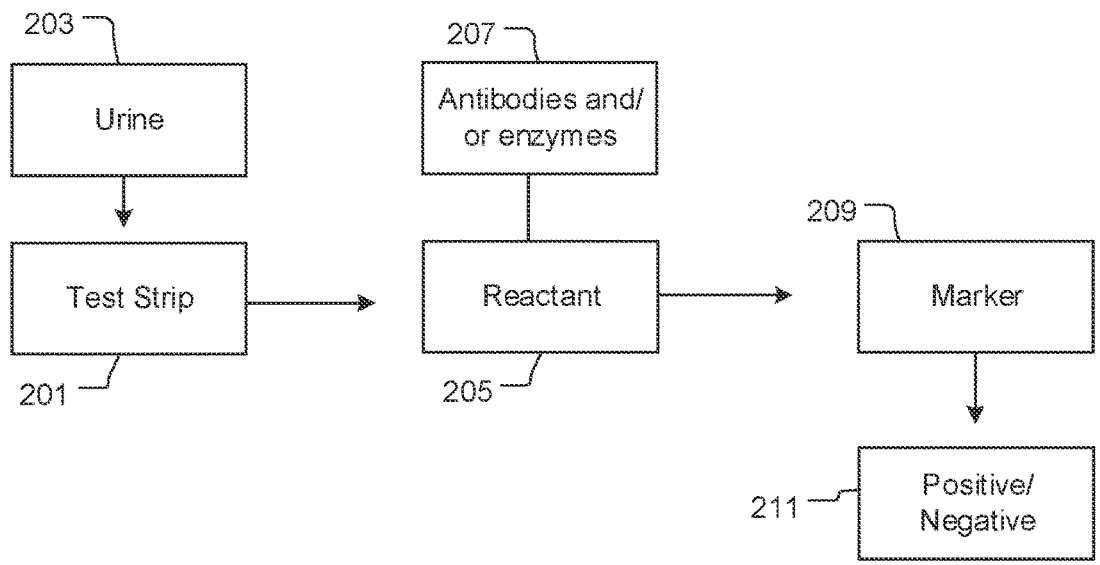
FIG. 2 is a simplified diagram of the features of one test of the testing system of the present application.

In FIG. 2, a simple diagram shows the core features of each test of the plurality of tests. Each test will include a test strip 201, which in the preferred embodiment will be configured to receive urine 203, the test strip 201 in fluid communication with a reactant 205. The reactant may vary, but in one embodiment it is contemplated that the reactant 205 includes antibodies and/or enzymes 207 that are fixed or embedded to the test strip such that they will bind to hCG to create a marker 209 to indicate a positive or negative result 211.

Figure 3:
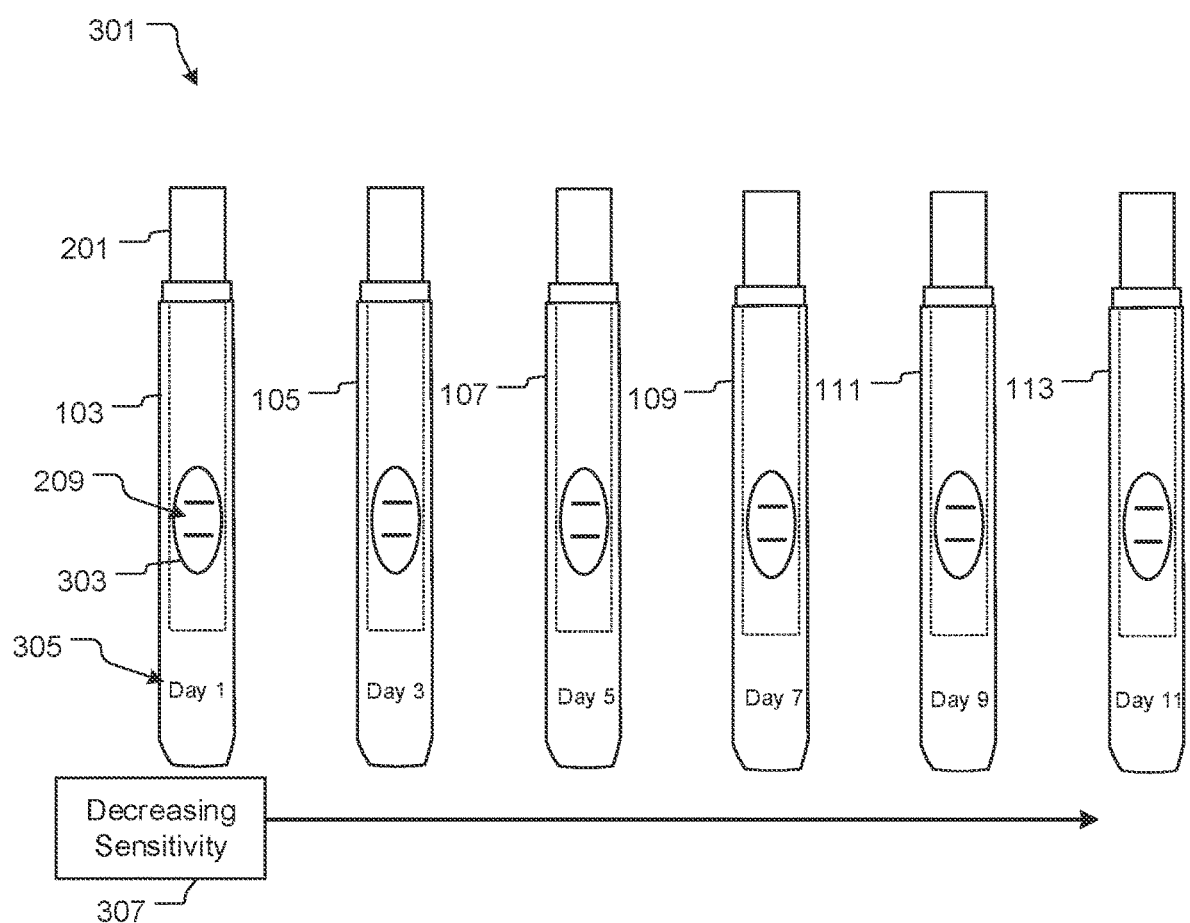
FIG. 3 is a front view of one contemplated plurality of tests of the test system of FIG. 1.

In FIG. 3, one exemplary embodiment of a system 301 is shown as it would be presented and used by the user. As shown, the system 301 will include the plurality of tests 103, 105, 107, 109, 111, 113 which will be packaged and sold together as a system. It is contemplated that the user may be provided with a plurality of "Day 1" tests, as the user may desire to take several "Day 1" tests with the highest sensitivity to achieve a first positive result. As shown, each test will include a test strip 201, a marker 209, and a viewing window 303. In addition, it is contemplated that each test may include a label 305 for labeling which day or sensitivity is associated with the test. This allows the user to easily take the tests in decreasing sensitivity 307.

Figure 4:
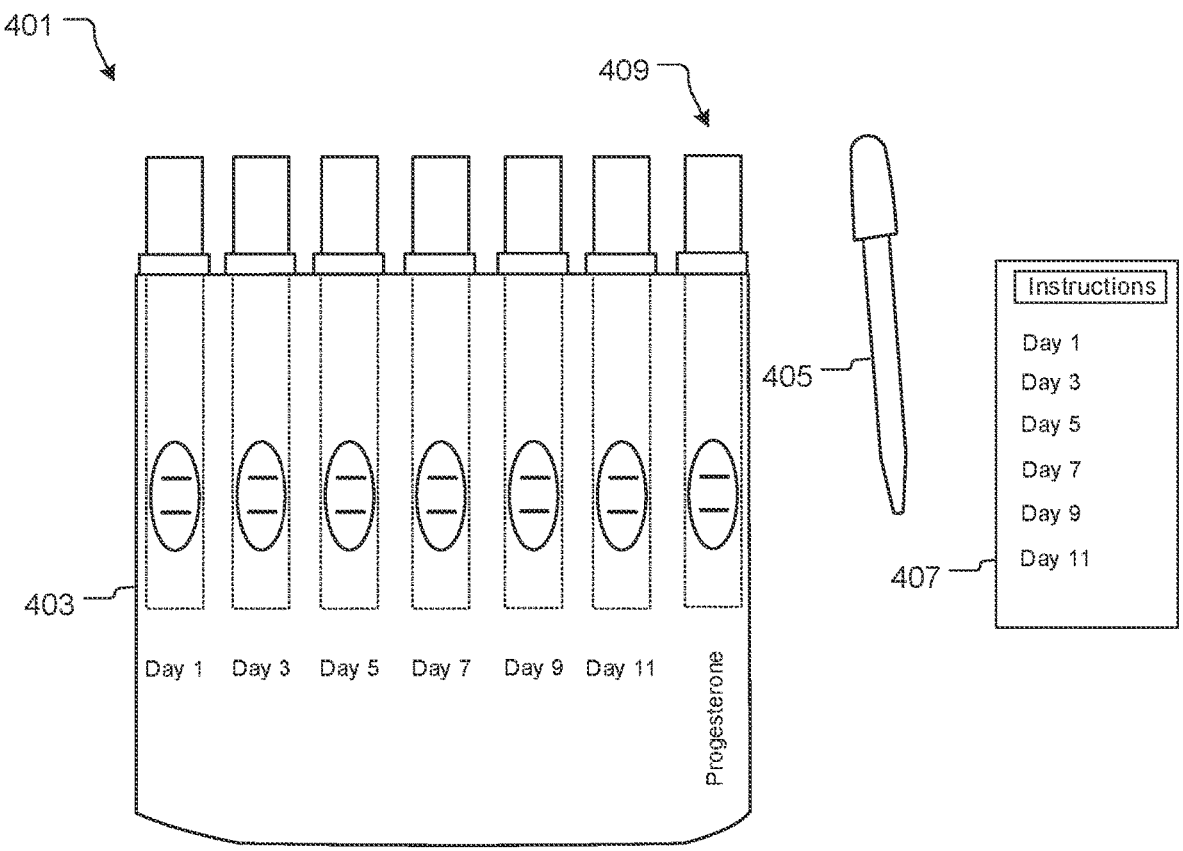
FIG. 4 is a front view of a second contemplated plurality of tests of the test system of FIG. 1.

In FIG. 4, a second embodiment of a testing system 401 is shown. In this embodiment, the user is provided with a single test 403 that includes the plurality of tests of decreasing sensitivity as discussed above. In this embodiment, as well as other embodiments, the user may also be provided with a dropper 405 and/or an instruction sheet 407. In this embodiment, as well as other embodiments, a progesterone test 409 may be included with the testing system, the progesterone test 409 providing a secondary indicator of a progressing pregnancy.

Figure 5:
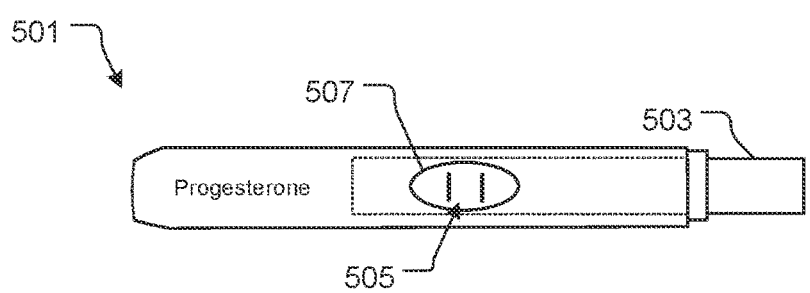
FIG. 5 is a front view of a progesterone test that can be used in conjunction with the system of FIG. 1.

In FIG. 5, an example of a progesterone test 501 is shown, which can be used in connection with the plurality of tests as discussed above to provide a secondary indicator of a progressing pregnancy. The progesterone test 501 will include a test strip 503 in fluid communication with a reactant 505 to provide positive of negative results 507.

Progesterone is made at the time of ovulation and remains elevated in the first trimester. This can be detected in blood and in the urine as the metabolite, pregnanediol glucuronide (PdG). Progesterone levels remain elevated once pregnancy is achieved and are also predictive of pregnancy viability in naturally conceived cycles where no exogenous hormones are given. The progesterone level does not change significantly, so this does not need to be followed sequentially, but would be incorporated as a onetime test.

Progesterone testing could also be taken as a set of three qualitative tests. Each test would be made to be positive at a level that would correlate to a serum level of 5, 10, and 20. Alternatively, this could also be done on more the more sophisticated digital meters. Statistically, a progesterone level>20 is highly predictive of viable pregnancy and levels<10 are at high risk for pregnancy loss, even more so if <5.

It should be appreciated that one of the unique features believed characteristic of the present application is the configuration of the plurality of tests to indicate an increase in hCG of the user, thereby indicating that the pregnancy is progressing.

Figure 6:
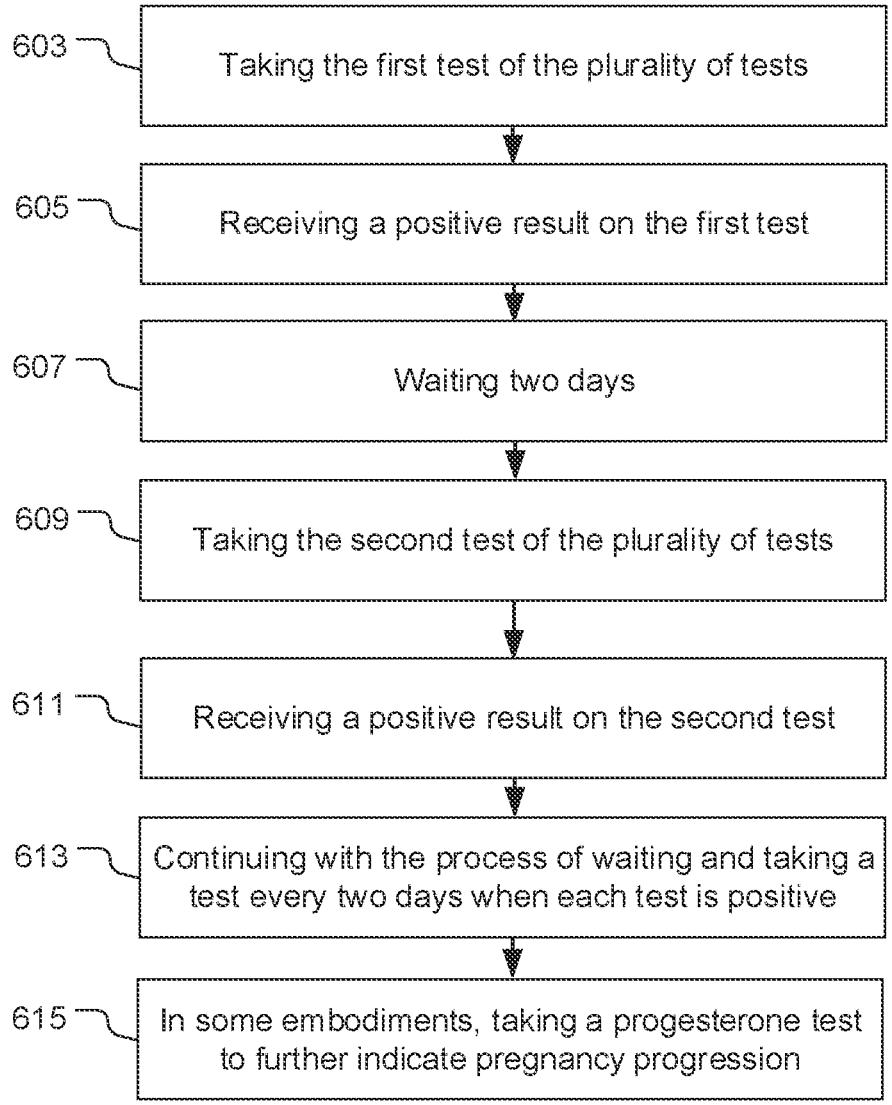
FIG. 6 is a flowchart of a method of use of the system of FIG. 1.

In FIG. 6, a flowchart 601 depicts a method of use of the system of the present invention. During use, the user will take one or more of the first tests until a positive result is achieved, as shown with boxes 603, 605. The user will then wait two days and take the second test, as shown with boxes 607, 609. If the user again gets a positive result, they will wait two more days to take the third test and continue with the process so long as they are getting positive results, as shown with boxes 611, 613. In some embodiments, the user can further take a progesterone test, as shown with box 615. If the user receives all positive tests and a positive progesterone test, they will have a better indication that their pregnancy is progressing.

Figure 7:
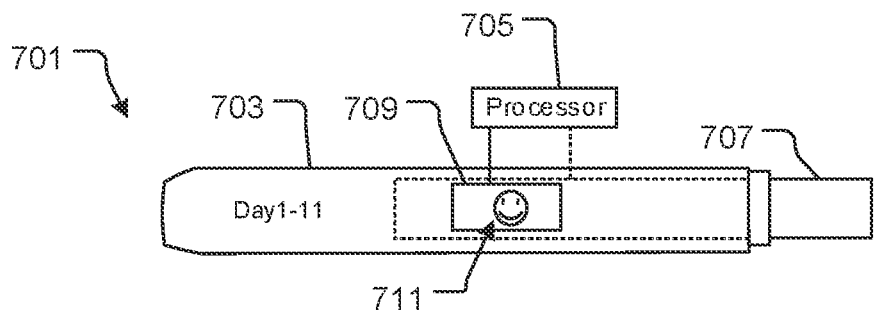
FIG. 7 is a front view of an alternative embodiment of a test which could replace the tests of the embodiments of the previous figures.

In FIG. 7, a view of an alternative embodiment of a test 701 is shown. Test 701 may replace each of the plurality of tests above and is similar in functionality, however, test 701 is a digital test, wherein a body 703 houses a processor 705 in communication with a test strip 707 and viewing window 709, wherein in this embodiment, the viewing window is a screen. The screen provides a marker 711 to provide positive or negative results. It should be appreciated that the marker may be a symbol of any sort. In some embodiments, the user will receive a plurality of tests as discussed above with decreasing sensitivity, wherein the tests provide digital results.

Figure 8:
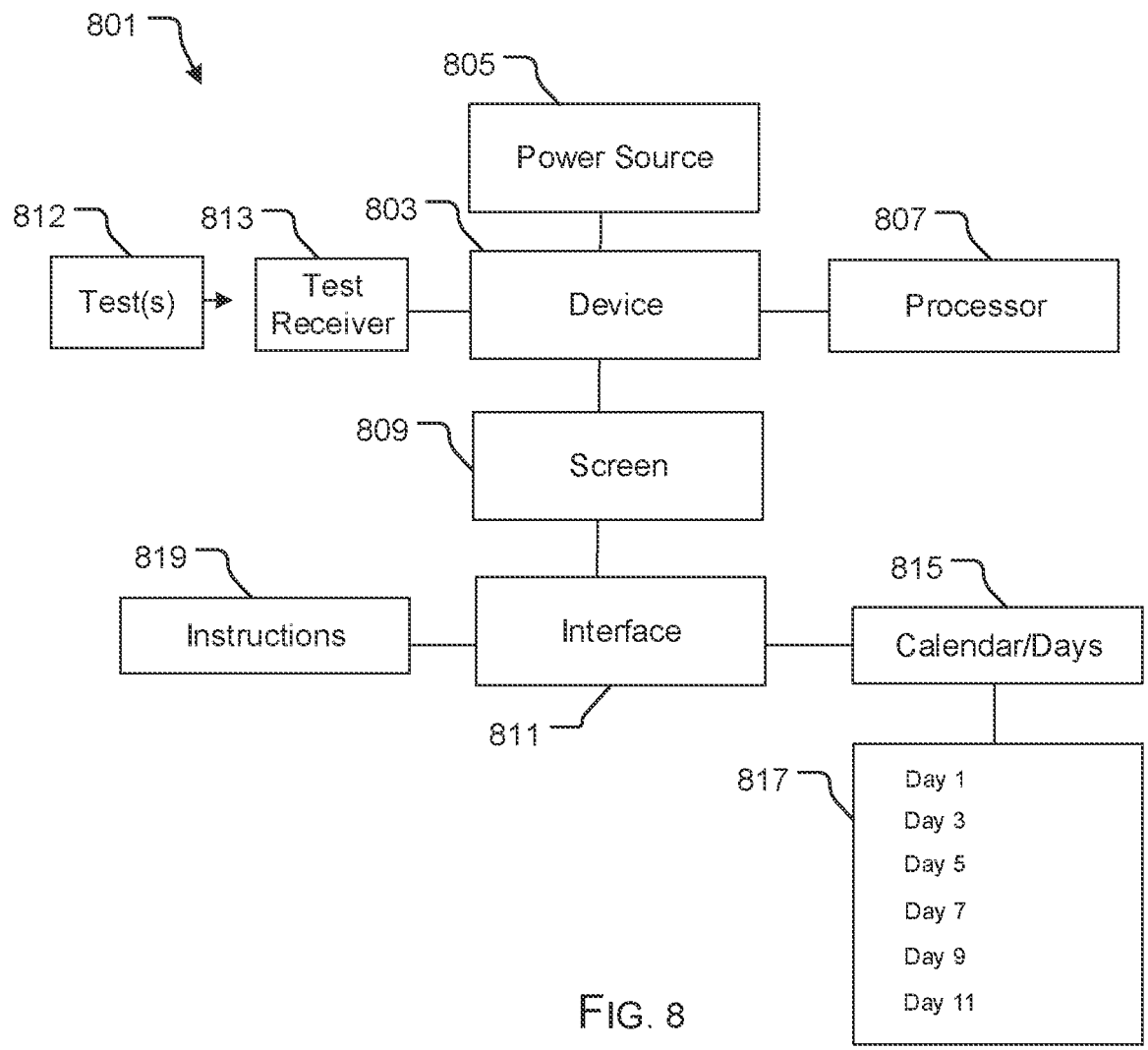
FIG. 8 is a diagram of an alternative embodiment of a test system of the present application.

In FIG. 8, a schematic of an alternative embodiment of a testing system 801 is shown. System 801 may include any of the features discussed above, and functions on the same premise, wherein the user will be provided with results based on decreasing sensitivity. System 801 includes a device 803 with a power source 805 and a processor 807, wherein the device may be handheld and will provide the user with a screen 809 and interface 811. In this embodiment, the user will utilize one or more tests 812, which may be similar to the tests discussed above having a test strip to receive a urine sample, the one or more tests 811 to be inserted into a test receiver 813 associated with the device. The device will then determine a positive or negative associated with the test to provide the user with results. It should be appreciated that the analysis of the test and sample could be completed in any known manner, such as discussed above. It should be appreciated that the results may be provided in any number of ways, such as via a calendar and/or day listing 815, 817. This embodiment may further include instructions 819 to direct the user to take certain tests on certain days. It should be appreciated that the overall functionality is the same, wherein the user will take a series of tests to determine if their pregnancy is likely progressing.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A home pregnancy testing viability system, consisting of:

a first test having a first test strip in communication with a first viewing window, a first marker presented on the first test strip to indicate positive or negative, a first antibody in fluid communication with the first test strip, the first antibody having a first sensitivity of approximately 20 mIU of human chorionic gonadotropin (hCG), and a first label stating day 1 marked on a top surface of the first test, wherein day 1 is the first day in which the user receives a positive result when taking the test having the approximately 20 mIU hCG sensitivity;

a second test having a second test strip in communication with a second viewing window, a second marker presented on the second test strip to indicate positive or negative, a second antibody in fluid communication with the second test strip, the second antibody having a second sensitivity of approximately 40 mIU of hCG, and a second label stating day 3 marked on a top surface of the second test;

a third test having a third test strip in communication with a third viewing window, a third marker presented on the third test strip to indicate positive or negative, a third antibody in fluid communication with the third test strip, the third antibody having a third sensitivity of approximately 80 mIU of hCG, and a third label stating day 5 on a top surface of the third test;

a fourth test having a fourth test strip in communication with a fourth viewing window, a fourth marker presented on the fourth test strip to indicate positive or negative, a fourth antibody in fluid communication with the fourth test strip, the fourth antibody having a fourth sensitivity of approximately 160 mIU of hCG, and a fourth label stating day 7 on a top surface of the third test;

a fifth test having a fifth test strip in communication with a fifth viewing window, a fifth marker presented on the fifth test strip to indicate positive or negative, a fifth antibody in fluid communication with the fifth test strip, the fifth antibody having a fifth sensitivity of approximately 320 mIU of hCG, and a fifth label stating day 9 on a top surface of the fifth test; and a sixth test having a sixth test strip in communication with a sixth viewing window, a sixth marker presented on the sixth test strip to indicate positive or negative, a sixth antibody in fluid communication with the sixth test strip, the sixth reactant antibody having a sixth sensitivity of approximately 640 mIU of hCG, and a sixth label stating day 11 on a top surface of the sixth test;

wherein a plurality of positive results associated with the first, second, third, fourth, fifth, and sixth tests indicate a progressing pregnancy; and wherein the first, second, third, fourth, fifth, and sixth test are packaged together.

2. A home pregnancy test viability system, consisting of:

a group of six tests, each test of the group of six tests having a test strip configured to receive a sample;

a device, being independent of the group of six tests, the device having a test strip receiver configured to receive each test of the group of six tests independently on a predetermined schedule, the predetermined schedule being a first test on day 1, a second test on day 3, a third test on day 5, a fourth test on day 7, a fifth test on day 9, and a sixth test on day 11;

a processor in communication with the test receiver to analyze the test strip to determine if the test strip tests positive for a predetermined level of human chorionic gonadotropin (hCG) as determined based on the predetermined schedule, the predetermined level of human chorionic gonadotropin (hCG) for the predetermined schedule being 20 mIU on day 1, 40 mIU on day 3, 80 mIU on day 5, 160 mIU on day 7, 320 mIU on day 9, and 640 mIU on day 11, wherein day 1 is the first day in which the user receives a positive result at 20 mIU hCG sensitivity; and a screen associated with the device, the screen displaying the predetermined schedule wherein results are provided on the screen indicating a potential progression in pregnancy based on the sample of each test of the group of six tests, and wherein the screen showing a six positive determinations of the group of six tests over the predetermined schedule is indicative of the potential progression in pregnancy.

* * * * *